United States Patent [19]

Macourt

[11] 4,136,951
[45] Jan. 30, 1979

[54] SEPARATION AND ANALYSIS OF PARTICLE COATINGS

[76] Inventor: Dennis J. C. Macourt, 21 Koonawarra Ave., Lindfield, Sydney, N.S.W., Australia

[21] Appl. No.: 739,110

[22] Filed: Nov. 5, 1976

[30] Foreign Application Priority Data

Nov. 28, 1975 [AU] Australia .............................. PC4104

[51] Int. Cl.² .......................... G01N 1/00; G01J 3/00
[52] U.S. Cl. ................................ 356/36; 23/230 EP; 55/17; 356/316
[58] Field of Search ............... 356/36, 85; 55/17, 447; 23/230 EP

[56] References Cited

U.S. PATENT DOCUMENTS 3,759,617   9/1973   Barringer .............................. 356/36

Primary Examiner—Vincent P. McGraw

[57] ABSTRACT

A method of separating chemical coatings from particles is disclosed which may be used in the aerial prospecting for minerals or the determination of the chemical constituents of a dried liquid coating.

The coating is volatized and ionized by passing the particle and its coating into a plasma. Separation is achieved by passing the particle through and beyond the plasma. The coating constituents may be spectroscopically analyzed by passing the coating constituents directly into a second plasma and viewing the light emitted therefrom.

18 Claims, 1 Drawing Figure

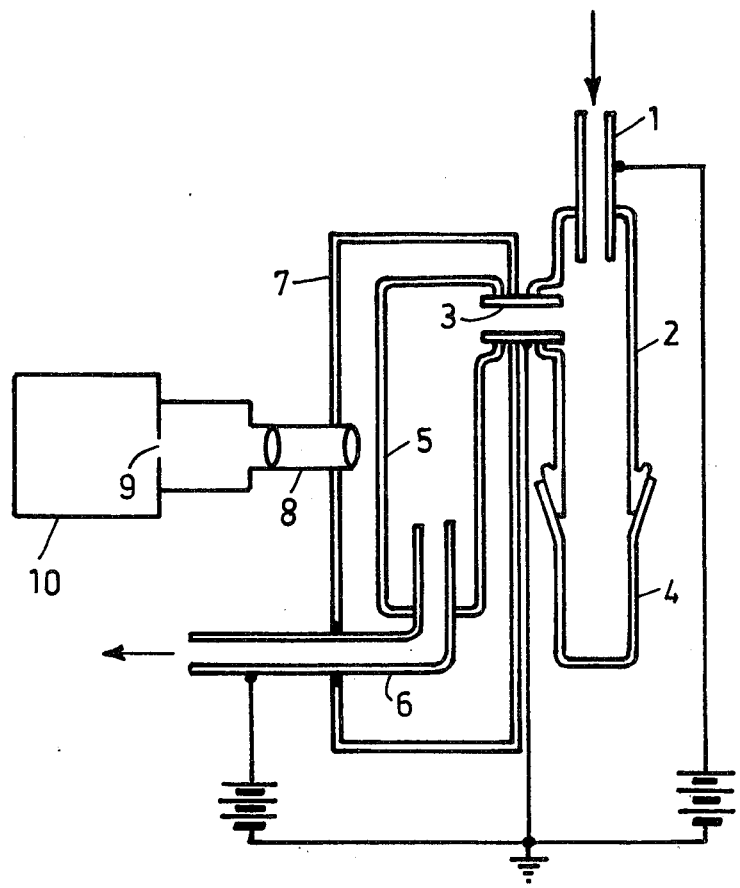

SEPARATION AND ANALYSIS OF PARTICLE COATINGS

The present invention relates to a method of separating a chemical coating from particles and provides a method of spectroscopically determining the chemical nature of any coating on particles. The invention has particular relevance to the aerial prospecting for both organically derived material and inorganic minerals, however, the invention is not limited thereto.

It is well known that the surfaces of small particles, such as dust particles, both on the ground and in the atmosphere can have coatings of different chemical composition to that of the particles themselves. This coating material, which is adsorbed on the surface of the particle, is the result of a variety of causes such as the evaporation of surface waters in the case of particles on the ground, or the agglomeration of condensation nuclei onto larger already airborne particles. The exact sources of such coatings and the processes involved in their creation are not fully understood. It is to be understood that the term "coating" covers a variety of possible combinations including individual, or numbers of, atoms or molecules adhering to the surface of a particle and, in addition, actual coatings in which the particle itself is partially or substantially completely covered or enveloped with a thin layer of a different material.

As the coating adsorbed onto the particles are representative of the geochemical, bacteriological and botanical characteristics of the region where the coatings are acquired, then chemical analysis of such coatings on particles sampled in different areas enables the geochemistry of these areas to be detected and determined. Further, since the major portion to the adsorbed coating material is generally water soluble, particles which are carried any distance from the original source of coating material will eventually lose that coating and acquire material related to a new location where it has a longer period of residence. Therefore there is a natural dilution of the original adsorbed coatings as particles are redistributed by wind and thermal action. However, in an area of anomalous chemistry or geochemistry, those particles which have the longest period of residence in the area, that is the larger particles, will still have a coating which is representative of the chemicals or minerals making up the anomaly.

These characteristics have been utilised in the high speed examination of large areas of ground for anomalous geochemical phenomena. In such an examination it is desirable to collect the larger particles, that is those having a dimension greater than 30 microns, which are in currents of rising air close to the surface of the ground. It is therefore possible to collect such particles by means of low flying aircraft and chemically analyse the nature of the particle coating in order to geologically map the area from which the particles were collected.

The analysis of the chemical coating of such particles may be carried out by conventional "wet" chemistry by dissolving the coating in a suitable solution and subsequently analysing the solution by such conventional methods as atomic absorption or atomic emission spectroscopy. Such conventional processes are slow and can only be applied in a batch operation since continuous processing is not possible. In addition such processes suffer from the large number of variables involved such as the strength of the solvent, its temperature and the time during which the particles are immersed in the solution.

It is also known to collect particles by means of their impingement on adhesive tape. The samples can then be analysed by means of a laser microprobe in which a controlled laser pulse is used to vaporise the particles on the tape and the released material is analysed. However this method is again a sample by sample process which is slow and expensive and only half the surface coating of the particles can be vaporised. In addition the method is subject to error because of trace elements in the tape and the tape adhesive.

One method of continuously analysing the chemical make-up of the particle coating would be to introduce the particles directly into a plasma and examine the light emitted by the plasma in a spectrometer. In this way all the surface coating would be vaporised and would emit a spectrum which was related to its chemical composition. Ideally, such a technique would enable the particles to be continuously analysed immediately after collection and thereby obviate the need for storage. Such spectral analysis requires that the particles be transferred into an inert gas such as helium or argon in a manner similar to that used in conventional spectrometers. This manner of transfer involves the projection of the particles into a counter-flowing stream of inert gas which at a predetermined point is reversed in direction of flow thereby acquiring the particles and transporting them to the desired region, in this case the plasma.

Such spectral analysis of such a plasma suffers from several drawbacks, however, the first of these drawbacks is that the temperature of the plasma, and hence the emission intensity of the lines being studied, varies in accordance with the thermal load presented to the plasma. This thermal load depends upon the size and frequency of the particles being introduced into the plasma and hence varies considerably. Therefore the temperature of the plasma varies greatly and so does the emission intensity of the lines.

Although this problem could be overcome by providing a high power plasma of several kilowatts in which the temperature of the plasma would be virtually unaffected by the thermal load presented to the plasma, such an approach is not a practical possibility in terms of the weight and power requirements of airborne equipment.

The second problem with the above-mentioned spectral analysis in that there is considerable interference with the individual weak lines, especially of molecular coatings, by strong lines produced by the particles themselves. Furthermore the physical size of the particles themselves and the limited field of view of the spectrometer can mask the emission of the coating itself. The foregoing, and in particular the presence of the particle itself in the plasma, produce unwanted emissions which may be of an intensity greater than the absolute level of the signal provided from the coating.

According to one aspect of the present invention there is disclosed a method of separating a chemical coating from particles, said method comprising the steps of;

1. Entrapping the coated particles in a flow of chemically inert carrier gas,

2. Plasmatising said carrier gas to volatilize and ionise said coating, and

3. Separating the particles from the volatilized and ionised coating constituents.

According to another aspect of the present invention there is disclosed a method of spectroscopically determining the chemical nature of any coating on particles, said method comprising the steps of;

1. Entraining the coated particles in a flow of chemically inert carrier gas,
2. Passing the carrier gas into a first plasma to volatilize and ionise the constituents of said coating,
3. Separating the particles from the volatilized and ionised coating constituents,
4. Including said volatilized and ionised coating constituents in a second plasma, and
5. Spectroscopically analysing the light emitted from said second plasma.

The present invention also includes within its scope apparatus for separating a chemical coating from particles, said apparatus comprising a primary plasma vessel, first and second tubular electrodes passing through the wall of said vessel and having their longitudinal axes mis-aligned, and a secondary plasma vessel communicating with said first plasma vessel via said second electrode and having a third tubular electrode passing through the wall thereof.

In addition the present invention also includes a method of prospecting using the above described methods or apparatus, and minerals found by means of the method of prospecting.

One embodiment of the present invention, and in particular the apparatus for carrying out the embodiment, will now be described with reference to the drawing. It is to be understood that the embodiment merely exemplifies the present invention and should not be construed in any limiting way.

The apparatus of the preferred embodiment comprises a primary plasma tube 2 having a first electrode tube 1 at one end and a particle receptacle 4 at the other. The particle receptacle 4 is detachable from the primary plasma tube 2 for emptying and a gas tight seal is able to be effected between the primary plasma tube 2 and the receptacle 4. A secondary plasma tube 5 communicates with the primary plasma tube 2 via a short length of tubing which forms a second electrode tube 3. The second electrode tube 3 is an electrode for both the primary plasma tube 2 and the secondary plasma tube 5. The second electrode tube 3 is preferably made from platinum or tungsten and has a length of approximately 5–10 m.m.

The secondary plasma tube 5 is located within a housing 7 which optically shields the second plasma tube 5 from the surroundings. A third electrode tube 6 is formed by a metal tube leading from the secondary plasma tube 5 out of the housing 7 and is connected to a vacuum pump, (not shown). The secondary plasma tube 5 is made of a transparent refractory material such as fused quartz. The interior of the secondary plasma tube 5 is able to be viewed by a spectrometer 10 comprising a diffraction slit or grating 9 coupled to the interior of the housing 7 by an optical system 8 formed from lenses, as illustrated, or optical fibres.

The second electrode 3 is connected to ground potential whilst the electrodes 1 and 6 are respectively connected to high voltage DC sources, each of which may have a different voltage. The DC sources may be of a conventional nature including current or voltage regulation and/or feedback.

The operation of the apparatus of the preferred embodiment will now be described with reference to the application of the present invention to prospecting for minerals. The size and power requirements of the apparatus are such as to enable the apparatus to be carried in an aircraft which may then be flown over the area to be prospected.

The aircraft samples the air over the area to be prospected and collects particles from the air. The particles are projected into a counter-flowing stream of chemically inert gas which, at a predetermined point, is reversed in direction of flow, thereby acquiring the particles and transporting them into the first electrode tube 1. The chemically inert gas is preferably helium or argon but such gas need not be restricted to a noble gas. As the gas enters the primary plasma tube 2 the presence of the electric field between electrodes 1 and 3 causes the gas to plasma and form a primary plasma between electrodes 1 and 3.

The extreme heat of the primary plasma volatilizes the coating adsorbed onto the particles and the volatilized constituents of the coating are ionised and form part of the primary plasma. Because of the mass of the particles, which generally have dimensions in excess of 30 microns, and their velocity of projection, the particles travel straight through the primary plasma and into the receptacle 4 where they are collected.

However the volatilized and ionised coating constituents being very much smaller than the particles are carried by the inert gas and therefore move in a 'J' shaped path into the electrode 3.

The extreme heat of the electrode 3 caused by the primary plasma prevents the ionised and volatilized constituents from plating out on the electrode 3. The volatilized and ionised coating constituents and the chemically inert carrier gas therefore pass through the electrode 3 and are introduced into the secondary plasma tube 5 where a secondary plasma is formed between electrodes 6 and 3. The coating constituents remain in the volatilized and ionised condition in the secondary plasma but the particles themselves have been separated from the coating constituents (as previously described) and therefore the particles are not present in the secondary plasma. The chemically inert gas prevents the coating constituents from undergoing any chemical reaction such as oxidization.

With the particles separated, the thermal load applied to the secondary plasma does not undergo large variations and therefore the temperature of the secondary plasma is maintained substantially constant. In additon there is no possibility of any particulate emission or fluorescence and therefore the emissions of the coating constituents in the secondary plasma are not masked by any extraneous emissions and thus the signal to noise ratio is greatly enhanced.

The light emitted from the secondary plasma is viewed by the spectroscope 10 and conventional spectroscopic analysis of the wavelengths emitted from the secondary plasma reveals the chemical make-up of and elements present in the coating constituents. In this way the nature of the coating may be readily and easily determined.

The velocity with which the particles are injected into the primary plasma tube 2 via the first electrode tube 1, the relative positioning of the first electrode tube 1 and the second electrode 3, and the bore of the second electrode 3, are so arranged that the particles continue on into the receptacle 4 whilst the chemically inert carrier gas and the vaporised ionised chemical constituents of the coating pass through the second electrode 3 and into the secondary plasma tube 5. The pressure within the secondary plasma tube 5 is reduced through the action of the vacuum pump (not shown) evacuating the secondary plasma tube 5 via the third electrode tube 6. This pumping permits accurate control of the gas flow to a constant level and thereby stabilises the plasma temperature and emission.

The apparatus preferably operates at a pressure at, or slightly below, atmospheric, for example in the range of 0.5 to 1.0 atmospheres, but it will operate above atmospheric pressure and at a very low pressure provided sufficient chemically inert gas is present to transport the particles into the primary plasma.

Clearly the electrodes and the plasma tubes should be constructed from materials that are free of those elements which are to be expected in the spectral analysis.

The above described apparatus is suitable for real time aerial prospecting for mineral deposits and geochemical anomalies.

In a further application of the present invention the chemical constituents of a liquid, for example a solution, may be determined spectroscopically. This may be performed by immersing small particles, such as small spheres of quartz, in the solution and then removing the particles and allowing the solution to dry on the surface of the particles. The particles may then be introduced into the above described apparatus, the coating removed from the particles and the emission spectrum of the solution constituents viewed spectroscopically. In this way not only are the emission lines of the solution constituents apparent without danger of masking by emission lines of the solvent (e.g. hydroxyl ion emissions), but if a tracer element such as a metal ion is added to the solution in a known concentration, such as 1ppm, then the relative intensities of the solution constituent emission lines lead directly to the concentration of each constituent in the original solution. Particles of quartz or silica are preferred because no part of such a particle enters the secondary plasma.

The foregoing describes only some applications and one embodiment of the present invention and modifications, obvious to those skilled in the art, may be made thereto without departing from the scope of the present invention. For example, the length of electrode tubes 1 and 6 may be adjustable and/or the plasma may be generated using AC including low frequency, RF or microwave frequencies rather than DC. In the case of RF or microwave frequencies being used the electrode tube discharge would be replaced by coils, waveguides or cavities generating a plasma. In this case the tubes themselves only fulfill a mechanical function of flow control and could be formed from a nonconductive material such as silica or an equivalent refractory material, however, the tube 3 would need to be optically opaque at the wavelengths being viewed to eliminate the possibility of light from the primary plasma being viewed by the spectrometer.

I claim:

1. A method of determining the nature of a chemical coating on particles, said method comprising the steps of:
   1. Entrapping the coated particles in a flow of chemically inert carrier gas,
   2. Plasmatising said carrier gas to volatilize and ionise said coating,
   3. Separating the particles from the volatilized and ionised coating constituents, and
   4. Analysing said volatilized and ionized coating constituents.

2. The method as claimed in claim 1 wherein said particles are separated from said volatilized and ionised constituents by retaining said constituents in a plasma and removing said particles from said plasma.

3. The method as claimed in claim 2 wherein said carrier gas included entrapped particles is introduced into said plasma in a first direction and said plasma moves said volatilized and ionised coating constituents in a second direction divergent from said first direction.

4. The method as claimed in claim 1 wherein said particles are entrapped in said carrier gas by projecting the particles into a counter-flowing stream of said gas and subsequently reversing the direction of flow of said gas.

5. The method as claimed in claim 1 wherein said carrier gas is nitrogen or a noble gas.

6. A method of prospecting for minerals comprising collecting particles from positions adjacent the locality to be prospected and subjecting the particles to the method claimed in claim 1.

7. The method as claimed in claim 6 wherein said particles are collected from the air by aircraft flying above said locality to be prospected.

8. A method of spectroscopically determining the chemical nature of any coating on particles, said method comprising steps of;
   1. Entraining the coated particles in a flow of inert carrier gas,
   2. Passing the carrier gas into a first plasma to volatilize and ionise the constituents of said coating,
   3. Separating the particles from the volatilized and ionised coating constituents,
   4. Including said volatilized and ionised coating constituents in a second plasma, and
   5. Spectroscopically analysing the light emitted from said second plasma.

9. The method claimed in claim 8 wherein said first plasma moves said volatilized and ionised coating constituents in a direction divergent from the direction of introduction of said carrier gas into said first plasma to separate said particles from said first plasma.

10. The method as claimed in claim 9 wherein the direction of motion of said volatilized and ionised coating constituents in said first plasma removes them from said first plasma and carries them into said second plasma.

11. The method as claimed in claim 8 wherein said second plasma is optically shielded from said first plasma.

12. A method of prospecting for minerals comprising collecting particles from positions adjacent the locality to be prospected and subjecting the particles to the method claimed in claim 8.

13. Apparatus for separating a chemical coating from particles, said apparatus comprising a primary plasma vessel, first and second tubular electrodes passing through the wall of said vessel and having their longitudinal axes mis-aligned, and a secondary plasma vessel communicating with said first plasma vessel via said second electrode and having a third tubular electrode passing through the wall thereof.

14. Apparatus as claimed in claim 13 including means to form plasma between said first and second electrodes and between said second and third electrodes.

15. Apparatus as claimed in claim 13 including means to introduce carrier gas into said primary plasma vessel via said first electrode and extract gas from said secondary plasma vessel via said third electrode.

16. Apparatus as claimed in claim 13 wherein said primary plasma vessel includes a particle receptacle disposed opposite to said first electrode.

17. Apparatus as claimed in claim 13 wherein said secondary plasma vessel is made from transparent material.

18. Apparatus as claimed in claim 17 wherein said secondary plasma vessel is optically shielded from the light emitted from any plasma in said primary plasma vessel.

* * * * *